May 7, 1974

V. J. DRAKE

Plant Pat. 3,542

MAPLE TREE

Filed Jan. 23, 1973

United States Patent Office

Plant Pat. 3,542
Patented May 7, 1974

3,542

MAPLE TREE

Virgil James Drake, Rte. 1, Hartford, Mich. 49057

Filed Jan. 23, 1973, Ser. No. 325,994
Int. Cl. A01h 5/12
U.S. Cl. Plt.—51 1 Claim

ABSTRACT OF THE DISCLOSURE

A maple tree of the *Acer rubrum* type, having distinctively colored leaves turning from green to a colored border through shades of blue violet to red and yellow.

BACKGROUND OF DISCLOSURE

The present invention relates to a new and distinct variety of maple tree, *Acer rubrum,* which was discovered by me in September 1967 in Van Buren County, Mich. The tree has novel autumn coloring characteristics, as will be pointed out more fully hereinafter.

The tree was discovered growing in a bed under my direct supervision and control. My attention was attracted to this particular tree because of the distinct color effects of the leaves. It was transplanted and asexually reproduced by me through budding, which shows that the characteristics and distinctions herein set forth come true to form and are established and transmitted through succeeding propagations.

BRIEF DESCRIPTION OF DRAWINGS

The accompanying drawings show typical specimens of the foliage at succeeding periods of time, depicted in color as nearly true as it is reasonably possible to make the same in a color illustration of this character.

DETAILED DESCRIPTION OF NEW VARIETY

The following ia a detailed description of my new variety, with color terminology in accordance with the color chart published by IPI Color Code (Imont Co.), except where general color terms of ordinary dictionary significance are obvious.

The tree has a size and shape of growth which compares generally with rubrum maple trees and holds its distinguishing characteristics through succeeding propagations by budding. The growth rate is rapid as compared with the species. The leaf shape, when juvenile, is quite elongated, resembling *Acer tataricum.* The instant variety has neither bloomed nor borne fruit.

It has been grown in Van Buren County, Mich., where the characteristics described have been observed.

Figure 1:
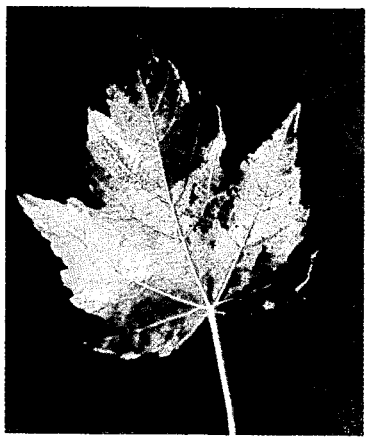
Figure 2:
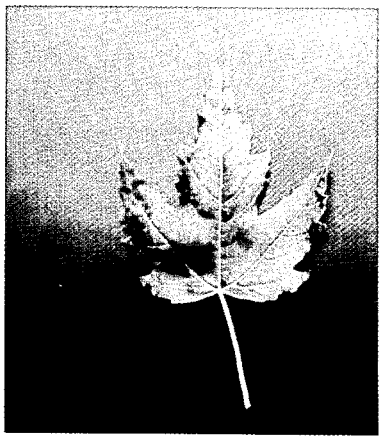
Figure 3:
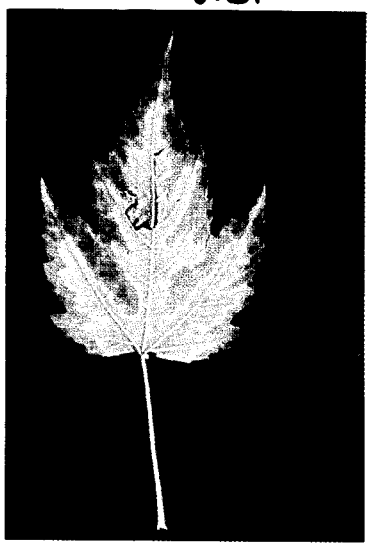
Figure 4:
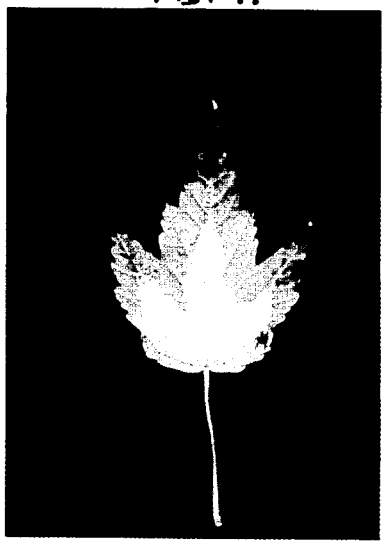
Figure 5:
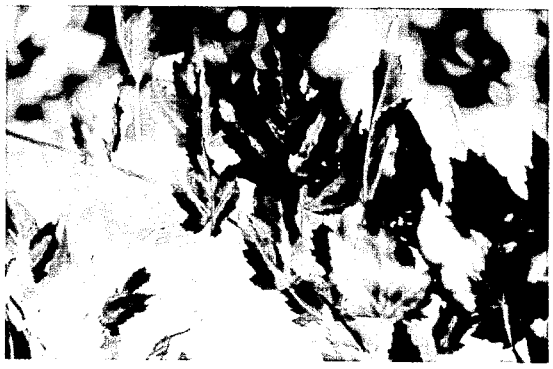

During normal growth and before changing to the distinctive colors herein described, the leaves have medium green, glossy foliage, comparable to other rubrum maples grown in the locality, as illustrated in FIG. 1 of the drawings, in the center portion thereof. Variations of color are depicted in the several other illustrations to show the succeeding changes. In this locality, the first change was observed about August 1, when the outside edge portion of the leaves turns to violet or blue violet (262), while the inside portion remains green (363). The outside portion continues to change until by September 10, the blue violet, outside edge portion of the leaves has been increased and the inside green area has been reduced, as shown in FIG. 2. These changes progress until by October 1 the variation in color is illustrated in FIG. 3, where the outside edge portion is red (187) and a green (363) inside portion is depicted. By October 10, the fourth variation depicted in FIG. 4 has occurred, where the outside edge portion is red (187) and the inside portion is yellow (824).

It will be apparent from these illustrations that the leaves have the normal green color of maple trees until early August, when they change gradually in a variation of color. The outside edges change from green to violet, then red, while the inside area changes from green to yellow, all at the normal fall color time.

This tree is especially desirable because of its distinctive color effects, being distinguished from other red maples grown under the same conditions in Van Buren County, Mich.

I claim:

1. A new and distinct variety of maple tree, substantially as herein shown and described, characterized particularly as to novelty by the unique combination of colors of its leaves which change as the fall season progresses from green throughout to an outer border portion which changes first to violet then to red and the inner portion changes from green to yellow as the tree ages.

No references cited.

ROBERT E. BAGWILL, Primary Examiner